US007817832B2

(12) United States Patent
Deinzer

(10) Patent No.: US 7,817,832 B2
(45) Date of Patent: Oct. 19, 2010

(54) METHOD FOR OPERATING AN X-RAY DIAGNOSTIC DEVICE FOR THE GENERATION OF HIGH-RESOLUTION IMAGES

(75) Inventor: Frank Deinzer, Röthenbach (DE)

(73) Assignee: Siemens Aktiengesellschaft, Munich (DE)

( * ) Notice: Subject to any disclaimer, the term of this patent is extended or adjusted under 35 U.S.C. 154(b) by 873 days.

(21) Appl. No.: 11/704,519

(22) Filed: Feb. 9, 2007

(65) Prior Publication Data

US 2007/0196009 A1 Aug. 23, 2007

(30) Foreign Application Priority Data

Feb. 10, 2006 (DE) ........................ 10 2006 006 449

(51) Int. Cl.
G06K 9/00 (2006.01)
(52) U.S. Cl. .................... 382/128; 382/294; 382/299
(58) Field of Classification Search ................. 382/128, 382/130, 132, 294, 299
See application file for complete search history.

(56) References Cited

U.S. PATENT DOCUMENTS

| 4,973,111 | A | | 11/1990 | Haacke et al. | |
|---|---|---|---|---|---|
| 5,649,032 | A | * | 7/1997 | Burt et al. | 382/284 |
| 6,618,468 | B2 | | 9/2003 | Klotz et al. | |
| 7,492,967 | B2 | * | 2/2009 | Toki et al. | 382/299 |

FOREIGN PATENT DOCUMENTS

| DE | 100 37 735 A1 | 2/2002 |
|---|---|---|
| DE | 101 19 105 A1 | 10/2002 |
| DE | 10 2005 010 119 A1 | 11/2006 |

OTHER PUBLICATIONS

Sina Farsiu, Dirk Robinson, Michael Elad, Peyman Milanfar, "Advances and Challenges in Super-Resolution", Wiley Periodicals, Inc., Mar. 15, 2004, pp. 47-57.
Sharon Peled and Yehezkel Yeshurun, "Superresolution in MRI: Application to Human White Matter Fiber Tract Visualization by Diffusion Tensor Imaging", Magnetic Resonance in Medicine, 2001, pp. 29-35, vol. 45, Wiley-Liss Inc.
Michael Elad and Arie Feuer, "Super-Resolution Reconstruction of Image Sequences", IEEE Transactions on Pattern Analysis and Machine Intelligence, Sep. 1999, pp. 817-834, vol. 21, No. 9.
Michael Elad and Arie Feuer, "Restoration of a Single Superresolution Image from Several Blurred, Noisy and Undersampled Measured Images", IEEE Transactions on Image Processing, Dec. 1997, pp. 1647-1658, vol. 6, No. 12.
Michal Irani and Shmuel Peleg, Super Resolution from Image Sequences, IEEE International Conference on Pattern Recognition (ICPR 90), 1990, pp. 115-120.
Athanasios Papoulis, "Generalized Sampling Expansion", IEEE Transactions on Circuits and Systems, Nov. 1977, pp. 652-654, vol. 24; No. 11.

* cited by examiner

Primary Examiner—Tom Y Lu

(57) ABSTRACT

The invention relates to a method for operating an X-ray diagnostic device with an X-ray source and an X-ray image detector with a sequence of images of low resolution single pictures with systems of coordinates that are different from each other being created, a harmonization of systems of coordinates of images being carried out, and finally a high resolution image being calculated from the images.

17 Claims, 5 Drawing Sheets

METHOD FOR OPERATING AN X-RAY DIAGNOSTIC DEVICE FOR THE GENERATION OF HIGH-RESOLUTION IMAGES

CROSS REFERENCE TO RELATED APPLICATIONS

This application claims priority of German application No. 10 2006 006 449.6 filed Feb. 10, 2006, which is incorporated by reference herein in its entirety.

FIELD OF THE INVENTION

The invention relates to a method for operating an X-ray diagnostic device with an X-ray source and an X-ray image detector.

BACKGROUND OF THE INVENTION

FIG. 1 shows an X-ray device of this kind, known from DE 100 37 735 A1, that has a C-arm 2, rotatably mounted on a stand 1, on the ends of which are mounted an X-ray beam 3 and an X-ray image detector 4.

Floor or ceiling mountings can also be used instead of the illustrated stand 1. The C-arm 2 can also be replaced by an electronic C-arm 2 with an electronic coupling of the X-ray beam 3 and X-ray detector 4.

The X-ray detector 4 can be a rectangular or square, flat semiconductor detector that preferably is made from amorphous silicon (aSi).

A patient couch 5 to support the patient to be examined is located in the path of the X-ray beam 3.

In X-ray diagnostics, high-resolution images are required as the basis of a safe and correct diagnosis. The object is to make the smallest detail visible at high quality. In X-ray diagnostics, the image quality is influenced mainly by the administered X-ray dose. The X-ray dose, however, mainly influences the image noise and the contrast of an X-ray image with, very generally speaking, a high X-ray dose producing a noise-free, strong-contrast image.

Just using flat image detectors (FD) alone has no effect on the resolution of an X-ray image. It depends essentially on the pixel resolution of the detector system.

Prior art consists of the use of zoom formats on C-arm systems to produce a high-resolution X-ray image. These methods do not use a complete X-ray image detector for image generation, but instead only a smaller part area so that the image appears enlarged. This process is, however, in the end limited by the existing resolution of the X-ray image amplifier (RBV) or flat detector (FD) and is not able to show anatomical details that are smaller than the physical resolution capability of the X-ray image detector. Furthermore, image interpolation methods that extrapolate the single images to a higher resolution, e.g. using bi-cubic interpolation, are not able to resolve details that are too small and therefore not visible.

The only way to improve the resolution capability is to make an expensive change to the X-ray image detectors of RBV and FD systems. This means that an improved X-ray image detector must offer in the same area 2048×2048 pixels instead of 1024×1024 pixels. This, however places a heavy requirement on detector manufacturers, already at the limits of what is currently technically possible, and on costs that a new image detector involves, not to mention the fact that the area of a single pixel, that reduces with an increase in the resolution, directly influences the X-ray quantum yield and thus, for example, also the noise in the X-ray image.

Altogether, the technical possibilities available for increasing the pixel resolution are very limited.

For this reason, the older patent application DE 10 2005 010 119.4 proposed changes to the source-image distance (SID) for present-day C-arm systems whereby a sequence of low-resolution images with a different source-image distance (SID) are produced, a harmonization of the systems of coordinates of the images is carried out and an image with a higher resolution, called a C-arm superresolution image, is calculated from the images. C-arm systems are, however, generally not the X-ray systems that are used for diagnostic purposes because they are too expensive and have too few features to create a normal X-ray image. The aforementioned C-arm solution, variation of the SID, simply cannot be used with present-day simple systems because with those the SID can generally not be varied.

Also in other areas in which images are taken, for example, with current video and photographic cameras, there is a similar problem. Therefore, it is not technically possible to increase the resolution of photographic cameras to order. In applications in which a greater degree of detail is required in the images, such as for example with satellite pictures and military reconnaissance pictures, methods called "Superresolution" have been known for a fairly long time that take several single pictures and from these calculate a single high-resolution image, such as is for example described in "Advances and Challenges in Super-Resolution" by Sina Farsiu et al., Invited Paper, International Journal of Imaging Systems and Technology, Special Issue on High Resolution Image Reconstruction, Vol. 14, No. 2, pages 47 to 57, 2004.

All that is available in the field of medicine is a description of the application of a superresolution method for the generation of high-resolution MRI images in "Superresolution in MRI: Application to Human White Matter Fiber Tract Visualization by Diffusion Tensor Imaging" by Sharon Peled et al., Magnetic Resonance in Medicine, 45, pages 29 to 35 (2001).

The functional principle of superresolution methods is based on the availability of a sequence of images consisting of several images as an input that can be registered against each other by an affine transformation. With satellite pictures or with video sequences taken by a video camera this affine transformation is, for example, provided by a shift of the scene in the image. This translation adequately meets the requirements of an affine transformation and is very easy to realize.

The general model of superresolution can according to M. Elad et al., "Super-Resolution Reconstruction of Image Sequences" IEEE Transactions on Pattern Analysis and Machine Intelligence, Vol. 21, No. 9, pages 817 to 834, September 1999, can be described as follows: Images $g_i$ of a low resolution of a sequence of images are the result of a projection P of a high-resolution image f on their image plane and a matching of their systems of coordinates by an affine 2-D transformation. Only the images with a low resolution can be observed, the high-resolution image cannot be observed because of the limited facilities of the camera. It therefore follows that the approach functions because, due to the affine transformation, the images $g_i$ are, and also must be, located in different systems of coordinates.

The principle of superresolution is now explained using FIG. 2. Each box, both large and small, represents a single pixel or a single image point. FIG. 2 shows a first image 6 with a low resolution with pixels 9 and also a second image 7 with a slightly smaller resolution, shifted in the x and y direction, that by means of a transformation are to be brought to an image 8 with a higher resolution having image points 10. In the high-resolution calculated image 8, the area of the image points 10 is too small, whereas they are too large in the pixels 9 of the low-resolution original images 6 and 7.

The offset of the systems of coordinates required for the superresolution is very easy to create for satellite and video pictures:

For satellite pictures
The satellite itself moves around the earth. The pictures that are taken are therefore offset relative to each other.
For video pictures
With hand-held cameras a suitable movement is very easy to achieve.

That means that in both cases a moving scene of images with low resolution forms the starting point for a high resolution image.

SUMMARY OF THE INVENTION

The object of the invention is to provide a method of the type named in the introduction that guarantees a maximum detectability of the smallest details in a simple manner even with simple X-ray systems.

The object is achieved according to the invention in that a sequence of images of single pictures offset relative to each other is produced with coordinate systems that differ from each other, in that a harmonization of the systems of coordinates of the images is carried out and that an image with a high resolution is calculated from the images.

The use of a superresolution method with an X-ray system enables an X-ray image quality to be obtained with a resolution that permits a degree of detail that at present can be achieved only with difficulty using other technical methods. It is thus possible to make anatomical structures or pathological changes visible that with present-day X-ray image detectors are simply too small. A superresolution image can be calculated in an advantageous manner from images with a low resolution by means of an affine 2-D transformation.

According to the invention, the method can include the following steps.

a) Generation of a series of X-ray images of a stationery object by varying the position and/or alignment.
b) Selection of any image as a reference image
c) Determination of the optimum affine transformations $$T_i = \begin{pmatrix} \cos(\alpha_i) & -\sin(\alpha_i) & x_i \\ \sin(\alpha_i) & \cos(\alpha_i) & y_i \\ 0 & 0 & 1 \end{pmatrix}$$

in homogenous coordinates consisting of an angle of rotation and a translation within the image plane for determining the parameters that with minimum error map the respective image on the reference image.

d) Transfer of all the images into a common coordinates system by means of the calculated transformations and
e) Superimposition of all images and calculation of a super-resolution image.

It has been shown to be advantageous if the angle of rotation and the translation are determined with sub-pixel accuracy.

The required changes to X-ray systems are easy to realize if a sequence of low-resolution single pictures offset, or rotated, relative to each other is created.

Alternatively, a sequence of images of low-resolution single pictures, some of the pictures of which are offset relative to each other with the remainder being rotated, is created.

According to the invention, a sequence of images of low-resolution single pictures, offset against each other and rotated at the same time, can also be created.

In an advantageous manner, the determination of the transformation that minimizes the dissimilarity for a suitable degree of similarity between images takes place:

$$T_i = \underset{T}{\operatorname{argmin}} d(T \otimes g_i, g_R)$$

(Let $\otimes$ be the operator that uses the transformation T on the image $g_i$)

In doing so, according to the invention the degree of similarity between the images can be determined by forming the sum of the amounts of all pixel differences. Furthermore, according to the invention, other useful measures of difference can be used.

It has been shown to be advantageous if the X-ray image detector has degrees of translational and/or rotational freedom.

BRIEF DESCRIPTION OF THE DRAWINGS

The invention is explained in more detail in the following with the aid of exemplary embodiments shown in the drawings. The drawings are as follows.

DETAILED DESCRIPTION OF THE INVENTION

To use the aforementioned superresolution method on general X-ray images, it is necessary to find a way in which an offset of single images relative to each other can be achieved. In contrast to the older patent application DE 10 2005 010 119.4, if possible no attempt should be made to achieve this as is the case with existing systems, but instead a general system property is described that enables the creation of superresolution images. The design cost for the solution should in this case be held within limits.

Figure 1:
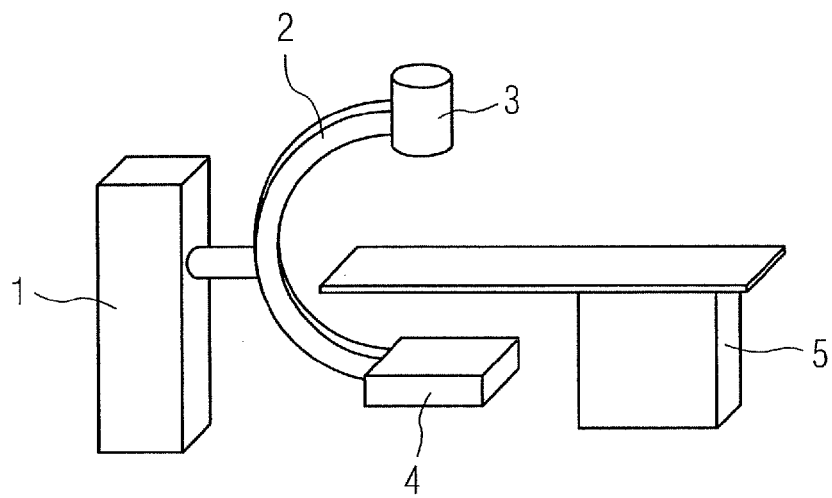
FIG. 1 A known X-ray diagnostic device
FIG. 2 Pictorial symbols to explain superresolution
FIG. 3 Construction of an X-ray diagnostic device according to the invention.
Figure 2:
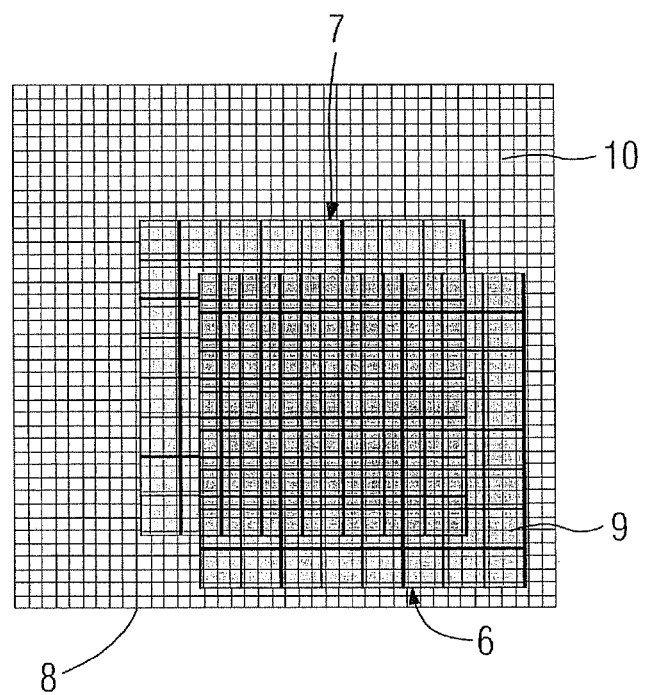
Figure 3:
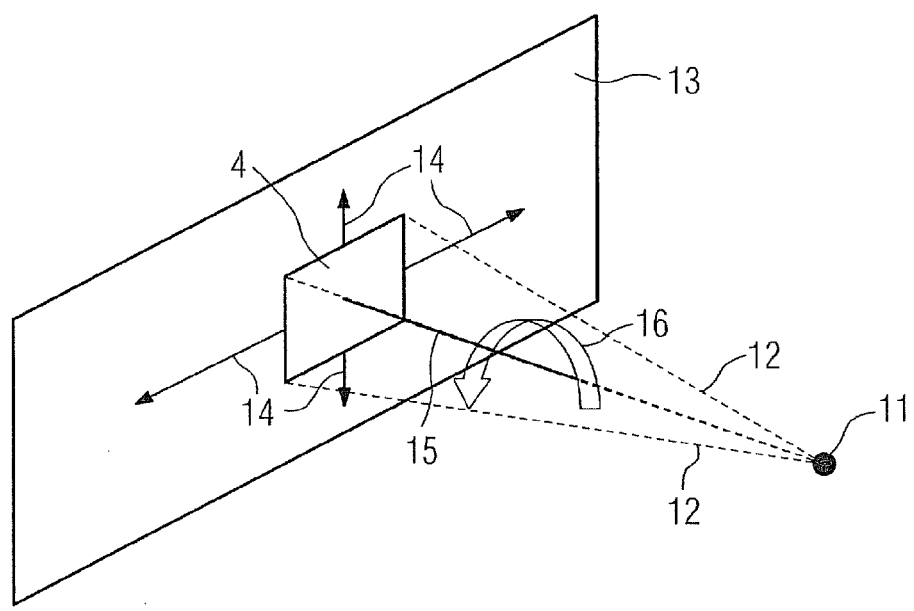

This is achieved by the construction of a general X-ray system with the required properties shown in FIG. 3.

An X-ray source 11 emits X-ray beams 12 that strike the X-ray image detector 4 located in a virtual image plane 13. In the process, the X-ray image detector 4 can be offset a small amount in the virtual image plane 13, as shown by arrow 14 that illustrates a possible translation within the image plane 13.

The impact point of the central beam of the X-ray source 11 normally corresponds to the centre vertical 15 of the X-ray image detector 4, around which the X-ray image detector 4 can be rotated by a small amount in the virtual image plane 13, as shown by arrow sixteen that illustrates a rotation vertical to the image plane 13.

Figure 4:
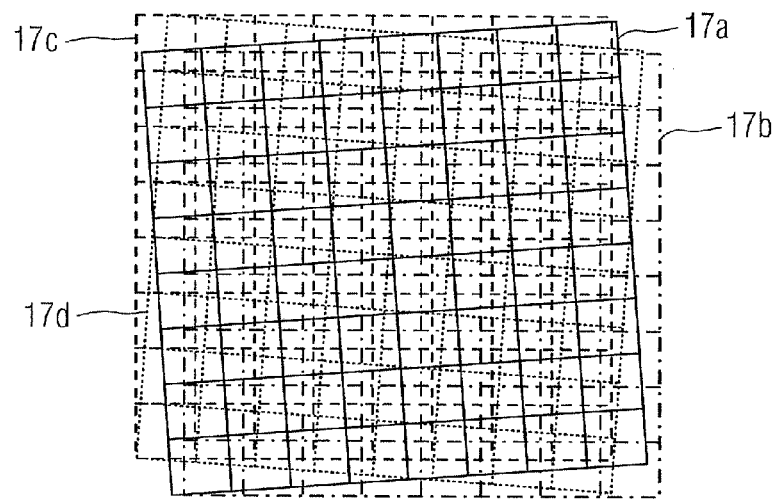
FIG. 4 Images, created by means of the arrangement shown in FIG. 3 that are offset and rotated relative to each other according to the invention.

By means of this arrangement, a sequence of images of low-resolution single pictures 17a to 17d offset and/or rotated relative to each other can be created by the X-ray image detector 4, as shown in FIG. 4.

The central aspect of general X-ray systems with the necessary properties required according to the invention for the creation of superresolution images is the X-ray image detector 4 that can be offset and/or rotated within a plane, so that both translational (xi, yi) degrees of freedom and/or the rotational ((($\alpha$i) degree of freedom result according to equation (1), i.e. the X-ray image detector 4 can easily move. In this case, the movement is limited on the plane in the space in which the image plane is located. For the degree of movement that the X-ray image detector 4 must have in order to be able to use the superresolution method, an offset or rotation by the width of a few pixels is sufficient. This means that

- a completely adequate translational freedom of movement of, for example, 10 pixels with a pixel size of 0.15 mm (for actual detector, see above), requires that the X-ray image detector 4 be able to be moved by a suitable mechanical construction by amounts of only 1.5 mm if possible in all directions according to the arrows 14,
- small movements are also sufficient for the degree of freedom of rotation. If, for example, the X-ray image detector 4 is enabled to move by only one degree around its centre, i.e. around its centre vertical 15, then a pixel offset of a good 20 pixels results in the edge areas of an X-ray image detector 4 with a 2500×2500 pixel size. Even with a 100 pixels next to the centre of rotation an adequate pixel offset of 1.7 pixels occurs.

Because the required movements are very small, present-day X-ray systems can also be fitted or retrofitted with suitable mechanical solutions that meet these movement requirements. Individual low-resolution pictures 17a to 17d of a sequence of images that arise with this arrangement are offset and rotated relative to each other according to FIG. 4.

If the general theoretical superresolution requirements are adapted, the following procedure results in the generation of high-resolution pictures.

1. Using the described degrees of freedom of movement, create a series of X-ray images $g_i$ of a stationary object or a stationery patient, where i=1 . . . N. These images are offset and/or rotated relative to each other (FIG. 4). Scaling does not occur.

2. Select any image $g_R$ as a reference image. Determine the optimum affine transformations $T_i$, $$T_i = \begin{pmatrix} \cos(\alpha_i) & -\sin(\alpha_i) & x_i \\ \sin(\alpha_i) & \cos(\alpha_i) & y_i \\ 0 & 0 & 1 \end{pmatrix} \quad (1)$$

in homogenous coordinates, consisting of the angle of rotation ($\alpha_i$) and the translation ($x_i$, $y_i$) within the image plane. This optimum transformation determines the parameters that map the respective image $g_i$ on the reference image $g_R$ with minimum error. This is not quite strictly correct which means that a transformation T is sought that minimizes the dissimilarity for a suitable similarity d(.,.) between images (e.g. sum of the amounts of all pixel differences):

$$T_i = \begin{pmatrix} \cos(\alpha_i) & -\sin(\alpha_i) & x_i \\ \sin(\alpha_i) & \cos(\alpha_i) & y_i \\ 0 & 0 & 1 \end{pmatrix} \quad (1)$$

(Let $\widehat{x}$ be the operator that uses the transformation T on the image $g_i$.)

Finally, the affine transformation acts like a resampling of the image. When doing so it should be noted that $\alpha_i$, $x_i$ and $y_i$ are to be determined with sub-pixel accuracy.

For $g_R = g_i$ the following naturally applies $$T_i = \begin{pmatrix} 1 & 0 & 0 \\ 0 & 1 & 0 \\ 0 & 0 & 1 \end{pmatrix}$$

The calculated transformations bring all the images together in a common coordinates system.

3. From the images laid over each other in that way, a superresolution image f that has a spatial 2-D resolution greater than in the single pictures 17 can be calculated on the basis of the redundant information, several images show the same image section in different resolutions. This step is generally known as image reconstruction, for which a whole series of works exists in literature.

The generalized sampling theorem, described by A. Papoulis in "Generalized Sampling Expansion", IEEE Transactions on Circuits and Systems, Vol. 24, No. 11, pages 652 to 654, November 1977.

The iterated backprojection, described by M. Irani and S. Peleg in "Super resolution from image sequences", International Conference on Pattern Recognition (ICPR 90), pages 115 to 120, 1990.

The maximum likelihood method and the maximum a-posteriori probability method described by M. Elad and A. Feuer in "Restoration of a Single Superresolution Image from Several Blurred, Noisy, and Undersampled Measured Images", IEEE Transactions on Image Processing, 6(12), pages 1646 to 1658, December 1997 and M. Elad and A. Feuer in "Superresolution reconstruction of an image" IEEE Transactions on Pattern Analysis and Machine Intelligence, 21, pages 817 to 834, 1999.

By means of this image reconstruction, details can be made visible that are not visible in any of the single pictures 17a to 17d; but are visible in the superresolution image because of the image reconstruction and the redundant information used.

Figure 5:
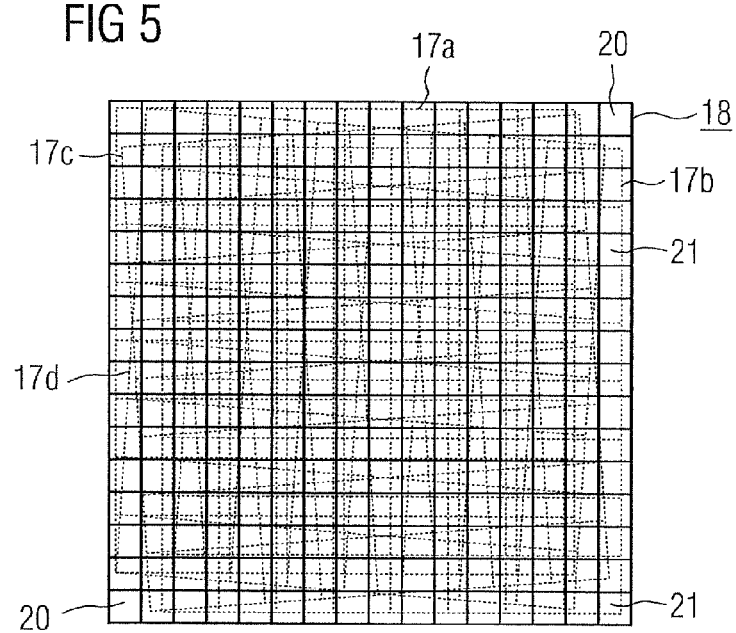
FIG. 5 A high-resolution image calculated from images shown in FIG. 4.

From the low-resolution single pictures 17a to 17d offset and/or rotated relative to each other, shown in FIG. 4, an X-ray image 18 with a high resolution can be created as is shown in FIG. 5.

Figure 6:
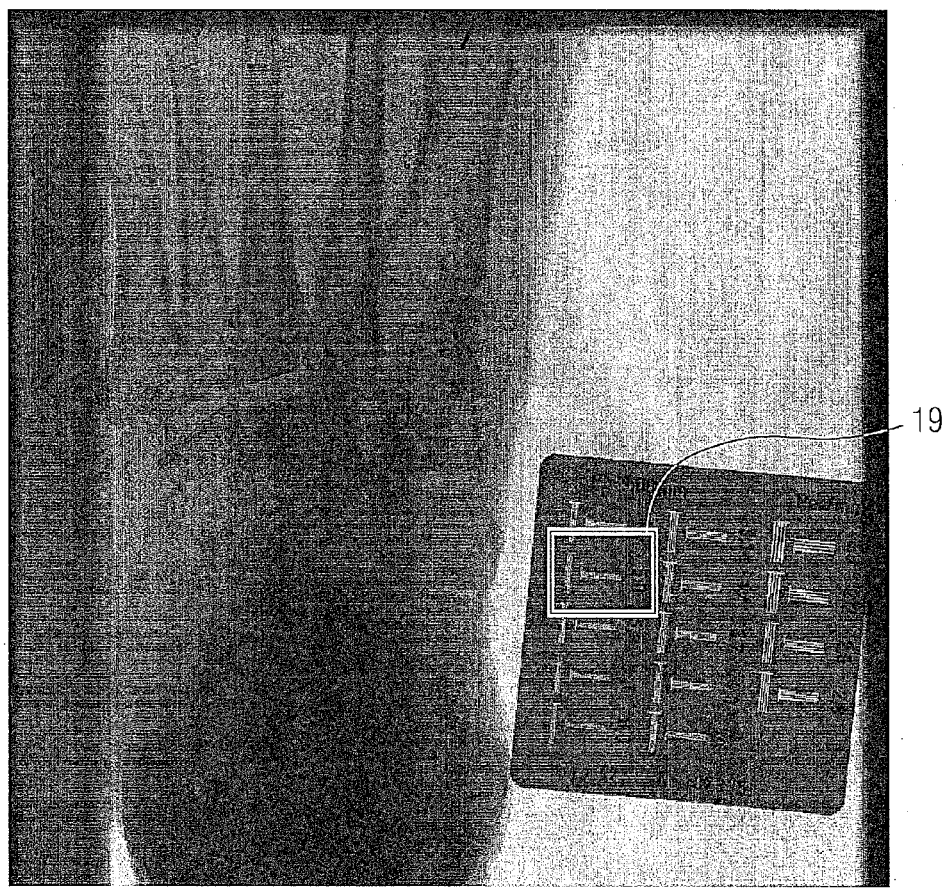
FIG. 6 An X-ray image with a resolution of 1024×1024 pixels
FIG. 7 A section of the X-ray image according to FIG. 6 and
FIG. 8 The same section from a high-resolution superresolution image.
Figure 7:
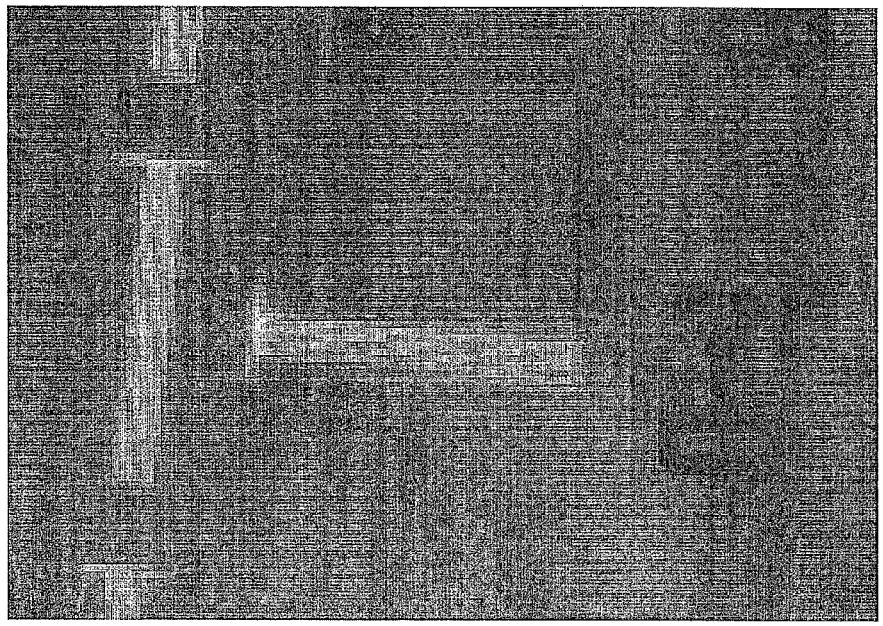

FIG. 6 shows a normal X-ray picture with a resolution of 1024×1024 pixels as is taken with present-day FD detectors. The marked section 19 is shown enlarged in FIG. 7 and shows that fine details of this kind cannot be reproduced with normal X-ray diagnostic equipment.

Figure 8:
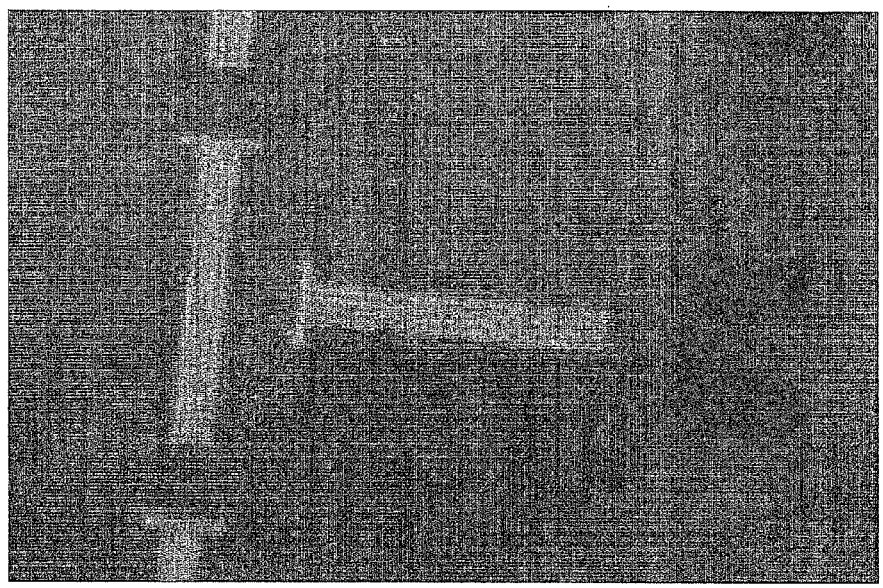

FIG. 8 shows the same section but of a calculated superresolution image. Thirty one input images of a quality according to FIG. 6 with the necessary image offset were available for this superresolution method, that lead to a substantial improvement in the spatial resolution with a corresponding gain in information.

When calculating the high resolution X-ray image 18, various areas with different information content occur:

Areas that are not visible in any single pictures 17a to 17d, such as for example the pixel 20 without information in FIG. 5 that is located in the edge that is not covered. No information is available here so that an area of this kind even if it is to be considered is shown as a homogenous monochrome area.

Areas that are visible only in a single picture, such as for example pixel 21 with information of only a single picture 17a to 17d in FIG. 5. Of course, in these areas the resolution can be increased, admittedly without an information gain. This means that no details are visible here that were not already visible in the single low-resolution picture 17b. Such methods for increasing the resolution are, e.g. a simple bi-linear interpolation. It should, however, be added that these image areas are small because of the relatively small movement area of the SID and because the object of interest to the attendant doctor will also be more or less centrally positioned.

Areas that are visible in all single pictures. In these areas the information gain will be fully obtained. This means that in the part of the X-ray image 18 details are visible that were not visible in any of the single pictures 17a to 17d. This is shown more clearly in the X-ray images in FIGS. 6 to 8. In the single pictures in FIGS. 6 and 7 the line structures are not visible in any of the low-resolution X-ray images. In the high-resolution superresolution image shown in FIG. 8 these line structures are, however, distinct, i.e. there is therefore really more information contained than in each single picture.

Areas present in some, more than one but not all, single pictures. Here it can generally be stated that the information gained, i.e. the final discernable improvement in resolution is that much greater the greater the number of images in an area.

To sum up it can be said that the resolution of the high-resolution X-ray image 18 is always equally as great and in principle can be chosen as required. The information content, i.e. the final visible structures, will however depend on how much information—how many low-resolution X-ray images 17a to 17d of the area were visible—is present for an area.

It has been shown that the use of a superresolution method for an X-ray system enables an X-ray image quality that with respect to its resolution permits a degree of detail that cannot at present be achieved with other technical possibilities. Using this makes anatomical structures or pathological changes visible that were simply too small for present-day X-ray detectors.

An important advantage is that the necessary changes to the X-ray systems are easy to realize due to the fact that the X-ray image detector 4 can be moved within very narrow limits. The movements required can, for example, be achieved using piezo actuators. The necessary image reconstruction can then be readily realized in the existing image system of the X-ray diagnostic equipment.

The invention claimed is:

1. A method for operating an x-ray diagnostic device comprising an x-ray source and an x-ray detector, comprising:

creating a sequence comprising a plurality of low resolution images, wherein the low resolution images comprises a plurality of coordinate systems that are different from each other;

performing a harmonization of the coordinate systems of the low resolution images, the harmonization, comprising:

selecting an image from the low resolution images as a reference image $g_R$, calculating the affine transformation $T_i$ for each image $g_i$ of the low resolution images as $$T_i = \begin{pmatrix} \cos(\alpha_i) & -\sin(\alpha_i) & x_i \\ \sin(\alpha_i) & \cos(\alpha_i) & y_i \\ 0 & 0 & 1 \end{pmatrix}$$

in a homogenous coordinate system consisting of an angle of rotation $\alpha_i$ and a translation $(x_i, y_i)$ within an image plane, determining a parameter that maps the image $g_i$ onto the reference image $g_R$ with a minimum error, and transferring the low resolution images to the homogenous coordinate system by the affine transformation calculating a high resolution image from the low resolution images after harmonizing the coordinate systems, wherein the harmonization of the coordinate systems is performed by an affine 2-D transformation, and wherein the sequence of the low resolution images are images of a stationery object under diagnosis and are offset or rotated relative to each other.

2. The method as claimed in claim 1, wherein the transferred low resolution images are superimposed by an image reconstruction and the high resolution image is calculated based on the superimposition.

3. The method as claimed in claim 1, wherein the angle of rotation and the translation are determined with sub-pixel accuracy.

4. The method as claimed in claim 1, wherein the transformation minimizes a dissimilarity for a suitable similarity between the images:

$$T_i = \underset{T}{\operatorname{argmin}}\, d(T \otimes g_i, g_R).$$

5. The method as claimed in claim 4, wherein a degree of similarity between the images is determined by summing all pixel difference in the images.

6. The method as claimed in claim 5, wherein the x-ray detector comprises translational or rotational degrees of freedom.

7. The method as claimed in claim 1, wherein the sequence of the low resolution images are offset relative to each other.

8. The method as claimed in claim 1, wherein the sequence of the low resolution images are rotated relative to each other.

9. The method as claimed in claim 1, wherein the sequence of the low resolution images comprises some images that are offset relative to each other and the remaining images that are rotated to each other.

10. The method as claimed in claim 1, wherein the sequence of the low resolution images are offset and rotated relative to each other at the same time.

11. A method for operating an x-ray diagnostic device comprising an x-ray source and an x-ray detector, comprising:

creating a sequence comprising a plurality of low resolution images of an object under diagnosis, wherein the low resolution images comprises a plurality of coordinate systems that are different from each other;

selecting an image from the low resolution images as a reference image $g_R$;

calculating an affine transformation $T_i$ for each image $g_i$ of the low resolution images as $$T_i = \begin{pmatrix} \cos(\alpha_i) & -\sin(\alpha_i) & x_i \\ \sin(\alpha_i) & \cos(\alpha_i) & y_i \\ 0 & 0 & 1 \end{pmatrix}$$

in a homogenous coordinate system consisting of an angle of rotation $\alpha_i$ and a translation $(x_i, y_i)$ within an image plane;

determining a parameter that maps the image $g_i$ onto the reference image $g_R$ with a minimum error;

transferring the low resolution images to the homogenous coordinate system by the affine transformation;

superimposing the transferred low resolution images; and calculating a high resolution image based on the superimposition.

12. The method as claimed in claim 11, wherein the object is a stationery object.

13. The method as claimed in claim 11, wherein the angle of rotation and the translation are determined with sub-pixel accuracy.

14. The method as claimed in claim 11, wherein the transformation minimizes a dissimilarity for a suitable similarity between the images:

$$T_i = \underset{T}{\mathrm{argmin}}\, d(T \otimes g_i, g_R).$$

15. The method as claimed in claim 14, wherein a degree of similarity between the images is determined by summing all pixel difference in the images.

16. An x-ray device for diagnosing an object with a high resolution image, comprising:

an x-ray source that emits an x-ray radiation passing through the object;

an x-ray detector that detects a plurality of low resolution x-ray images of the object, wherein the low resolution images comprises a plurality of coordinate systems that are different from each other; and an imaging processing unit that:

selects an image from the low resolution images as a reference image $g_R$, calculates an affine transformation $T_i$ for each image $g_i$ of the low resolution images as $$T_i = \begin{pmatrix} \cos(\alpha_i) & -\sin(\alpha_i) & x_i \\ \sin(\alpha_i) & \cos(\alpha_i) & y_i \\ 0 & 0 & 1 \end{pmatrix}$$

in a homogenous coordinate system consisting of an angle of rotation $\alpha_i$ and a translation $(x_i, y_i)$ within an image plane, determines a parameter that maps the image $g_i$ onto the reference image $g_R$ with a minimum error, transfers the low resolution images to the homogenous coordinate system by the affine transformation, superimposes the transferred low resolution images, and calculates the high resolution image based on the superimposition.

17. The x-ray device as claimed in claim 16, wherein the affine transformation minimizes a dissimilarity for a suitable similarity between the images:

$$T_i = \underset{T}{\mathrm{argmin}}\, d(T \otimes g_i, g_R)$$

and wherein a degree of similarity between the images is determined by summing all pixel difference in the images.

* * * * *